(12) United States Patent
Lanza et al.

(10) Patent No.: US 7,279,150 B2
(45) Date of Patent: Oct. 9, 2007

(54) CHELATING AGENTS WITH LIPOPHILIC CARRIERS

(75) Inventors: Gregory M. Lanza, St. Louis, MO (US); Samuel A. Wickline, St. Louis, MO (US); Phillip S. Athey, Lake Jackson, TX (US); Gyongyi Gulyas, Lake Jackson, TX (US); Garry E. Kiefer, Lake Jackson, TX (US)

(73) Assignees: Barnes-Jewish Hospital, St. Louis, MO (US); The Dow Chemical Corporation, Midland, MI (US)

( * ) Notice: Subject to any disclaimer, the term of this patent is extended or adjusted under 35 U.S.C. 154(b) by 580 days.

(21) Appl. No.: 10/765,299

(22) Filed: Jan. 26, 2004

(65) Prior Publication Data

US 2004/0248856 A1 Dec. 9, 2004

Related U.S. Application Data

(63) Continuation-in-part of application No. 10/351,463, filed on Jan. 24, 2003.

(60) Provisional application No. 60/485,970, filed on Jul. 9, 2003, provisional application No. 60/351,390, filed on Jan. 24, 2002.

(51) Int. Cl.
*A61B 5/0555* (2006.01)
*A61K 51/00* (2006.01)

(52) U.S. Cl. ............ 424/9.361; 424/9.3; 424/9.34; 424/9.36; 424/9.364; 424/1.11; 424/1.37; 424/1.49; 424/1.53

(58) Field of Classification Search ........... 424/9.3, 424/9.321, 9.322, 9.323, 1.11, 1.21, 1.37, 424/1.77, 9.361, 9.34, 9.36, 9.364
See application file for complete search history.

(56) References Cited

U.S. PATENT DOCUMENTS

| | | | |
|---|---|---|---|
| 5,064,636 A | 11/1991 | Li et al. | 424/9 |
| 5,120,527 A | 6/1992 | Li et al. | 424/9 |
| 5,512,294 A | 4/1996 | Li et al. | 424/450 |
| 5,571,498 A | 11/1996 | Cacheris et al. | 424/9.365 |
| 5,573,752 A | 11/1996 | Ranganathan et al. | 424/9.363 |
| 5,614,170 A | 3/1997 | Cacheris et al. | 424/9.365 |
| 5,690,907 A | 11/1997 | Lanza et al. | 424/9.5 |
| 5,780,010 A | 7/1998 | Lanza et al. | 424/9.32 |
| 5,804,164 A | 9/1998 | Elgavish | 424/9.364 |
| 5,958,371 A | 9/1999 | Lanza et al. | 424/1.21 |
| 5,989,520 A | 11/1999 | Lanza et al. | 424/9.32 |
| 6,010,682 A | 1/2000 | Unger et al. | 424/9.361 |
| 6,056,939 A | 5/2000 | Desreux et al. | 424/1.65 |
| 6,132,764 A | 10/2000 | Li et al. | 424/450 |

FOREIGN PATENT DOCUMENTS

| | | |
|---|---|---|
| WO | WO99/58162 | 11/1999 |
| WO | WO 00/35488 | 6/2000 |
| WO | WO 00/35492 | 6/2000 |
| WO | WO 00/35887 | 6/2000 |
| WO | WO 02/060524 | 8/2002 |
| WO | WO-02/076491 | 10/2002 |

OTHER PUBLICATIONS

Grant, C. et al., Magnetic Resonance in Medicine, 1989, 11, p. 236-243.*
Arbuzova et al., Biochimica et Biophysica Acta (2000) 1464(1):35-48.
Asuncion-Punzalan et al., Biochemistry (1998) 37(13):4603-4611.
Bittman et al., Biochemistry (1985) 24(6): 1403-1409.
Compton et al., Journal of Physical Chemistry (1994) 98(27):6818-6825.
Mayer et al., European Journal of Organic Chemistry (1999) 10:2563-2571.
Sänger et al., Bioconjugate Chemistry (1992) 3(4):308-314.
Shao et al., Drug Delivery (1997) 4(1):43-48.
Smith et al., EMBO Journal (2001) 20(13):3322-3332.
Supplementary European Search Report for EP 04705340.0, mailed on Jun. 13, 2007, 5 pages.

* cited by examiner

*Primary Examiner*—Michael G. Hartley
*Assistant Examiner*—Leah Schlientz
(74) *Attorney, Agent, or Firm*—Morrison & Foerster LLP

(57) ABSTRACT

Compounds useful for associating with nanoparticle or microparticle emulsions to obtain magnetic resonance images permit control of the relaxivity of the signal and readily associate with the particulate components.

22 Claims, 5 Drawing Sheets

Gd-MeO-DOTA-NCS

Gd-MeO-DOTA-PA

CHELATING AGENTS WITH LIPOPHILIC CARRIERS

CROSS-REFERENCE TO RELATED APPLICATIONS

This application is a continuation-in-part of U.S. Ser. No. 10/351,463, filed 24 Jan. 2003, which claims benefit from U.S. Ser. No. 60/351,390, filed 24 Jan. 2002. This application also claims benefit of provisional application 60/485,970, filed 9 Jul. 2003. The contents of these applications are incorporated herein by reference.

ACKNOWLEDGEMENT OF GOVERNMENT SUPPORT

This invention was supported in part by a grant from the U.S. Government. The U.S. Government has certain rights in this invention.

TECHNICAL FIELD

The invention is directed to chelating agents useful to support metal ions employed in magnetic resonance imaging (MRI) where the chelate is supplied in a carrier which comprises lipophilic particles or droplets. More specifically, the invention is directed to chelating agents coupled, optionally through a spacer, to phosphoglycerides.

BACKGROUND ART

The use of chelating agents of various types to entrap metal ions useful in magnetic resonance imaging is well known. Generally, the chelating agents contain a substantial number of unshared electron pairs or negatively charged or potentially negatively charged species. Perhaps the simplest among these is ethylenediaminetetraacetic acid (EDTA) commonly used as a water softener. However, many such agents are known, including, most notably, and commonly used, diethylene triamine pentaacetic acid (DTPA) and tetraazacyclododecanetetraacetic acid (DOTA) and their derivatives. U.S. Pat. Nos. 5,573,752 and 6,056,939, incorporated herein by reference, disclose particularly useful derivatives of DOTA which are coupled to a benzyl or phenyl moiety wherein the phenyl ring is substituted by isothiocyanate. This isothiocyanate provides a reactive group for coupling to various additional compounds. As described in these patents, the isothiocyanate group can be used to couple the chelate to a targeting agent such as an antibody or fragment thereof.

There is an extensive literature on delivery vehicle compositions that have been used to administer chelated metals for MRI. Some of these compositions do not contain targeting agents, though others do comprise such agents. For example, U.S. Pat. Nos. 5,690,907; 5,780,010; 5,989,520; 5,958,371; and PCT publication WO 02/060524, the contents of which are incorporated herein by reference, describe emulsions of perfluorocarbon nanoparticles that are coupled to various targeting agents and to desired components, such as MRI imaging agents, radionuclides, and/or bioactive agents. Other compositions that have been used for targeted imaging include those disclosed in PCT publications WO 99/58162; WO 00/35488; WO 00/35887; and WO 00/35492. The contents of these publications are also incorporated herein by reference.

The present invention in one embodiment is focused on improvements in the contrast agents useful in magnetic resonance imaging; some background information on this technique is appropriate in understanding the approach taken by applicants.

Magnetic resonance imaging (MRI) has become a useful tool for diagnosis and for research. The current technology relies on detecting the energy emitted when the hydrogen nuclei in the water contained in tissues and body fluids returns to a ground state subsequent to excitation with a radio frequency. Observation of this phenomenon depends on imposing a magnetic field across the area to be observed, so that the distribution of hydrogen nuclear spins is statistically oriented in alignment with the magnetic field, and then imposing an appropriate radio frequency. This results in an excited state in which this statistical alignment is disrupted. The decay of the distribution to the ground state can then be measured as an emission of energy, the pattern of which can be detected as an image.

While the above described process is theoretically possible, it turns out that the relaxation rate of the relevant hydrogen nuclei, left to their own devices, is too slow to generate detectable amounts of energy, as a practical matter. In order to remedy this, the area to be imaged is supplied with a contrast agent, generally a strongly paramagnetic metal, which effectively acts as a catalyst to accelerate the decay, thus permitting sufficient energy to be emitted to create a detectable bright signal. To put it succinctly, contrast agents decrease the relaxation time and increase the reciprocal of the relaxation time—i.e., the "relaxivity" of the surrounding hydrogen nuclei.

Two types of relaxation times can be measured. $T_1$ is the time for the magnetic distribution to return to 63% of its original distribution longitudinally with respect to the magnetic field and the relaxivity $\rho_1$, is its reciprocal. $T_2$ measures the time wherein 63% of the distribution returns to the ground state transverse to the magnetic field. Its reciprocal is the relaxivity index $\rho_2$. In general, the relaxation times and relaxivities will vary with the strength of the magnetic field; this is most pronounced in the case of the longitudinal component.

Thus, a desirable characteristic of any contrast agent is to provide the signal with an enhanced relaxivity both for $\rho_1$ and $\rho_2$. The present invention provides such contrast agents.

It is also advantageous to facilitate the excretion of the paramagnetic ion, which may otherwise be toxic if it is retained in a subject. Thus, it would be advantageous to provide a mechanism for cleaving the chelated metal ion from the particles or from any lipid components that might result in cellular or liver uptake.

There is an extensive literature regarding contrast agents which are based on chelated paramagnetic metals. For example, U.S. Pat. Nos. 5,512,294 and 6,132,764 describe liposomal particles with metal chelates on their surfaces as MRI contrast agents. U.S. Pat. Nos. 5,064,636 and 5,120,527 describe paramagnetic oil emulsions for MRI in the gastrointestinal tract. U.S. Pat. Nos. 5,614,170 and 5,571,498 describe emulsions that incorporate lipophilic gadolinium chelates, e.g., gadolinium diethylenetriaminepentaacetic acid-bisoleate (Gd-DTPA-BOA) as blood pool contrast agents.

U.S. Pat. No. 5,804,164 describes water-soluble, lipophilic agents which comprise particularly designed chelating agents and paramagnetic metals. U.S. Pat. No. 6,010,682 and other members of the same patent family describe lipid soluble chelating contrast agents containing paramagnetic metals which are said to be able to be administered in the form of liposomes, micelles or lipid emulsions.

Thus, in general, contrast agents may take the form of paramagnetic metals such as rare earth metals or iron mobilized in a form that permits substantial concentrations of the paramagnetic metal to be delivered to the desired imaging area.

One method for providing useful concentrations of contrast agents has been described by the present applicants in U.S. Pat. Nos. 5,780,010 and 5,909,520. A nanoparticle is formed from an inert core surrounded by a lipid/surfactant coating. The lipid/surfactant coating can then be modified to couple the particle to a chelating agent containing a paramagnetic metal. In addition, the particle can be coupled to a ligand for targeting to a specific site.

The present invention in one aspect provides an improvement in the design of contrast agents whereby the relaxivity of the signal can be controlled, and excretion can be facilitated. The compounds of the invention, however, are useful in other contexts as well, such as delivering radionuclides to desired locations for imaging based on nuclear emissions.

DISCLOSURE OF THE INVENTION

The invention provides compounds which can readily be associated with carriers of a variety of lipophilic delivery vehicles such as liposomes, fluorocarbon nanoparticles, oil droplets, and the like in a position relative to these delivery vehicles that provides for control of relaxivity of the signal and also provides, if desired, a mechanism for facilitating excretion of the potentially toxic paramagnetic ion that enhances the resonance image. In an alternative to chelation of a paramagnetic ion, a radioactive nuclide may be included; the desirability of facilitating excretion of this nuclide is also apparent. The paramagnetic ion or radionuclide is provided in a chelate contained in compounds of the formula:

$$\begin{array}{c}Ch\\|\\(CH_2)_m\\|\\(R^1)_l-\underset{}{\bigcirc}-NH\overset{Z}{\underset{\|}{C}}-NR^2-(spacer)_n-OP(O)_2-O-CH_2-CH-CH_2\\\qquad\qquad\qquad\qquad\qquad\qquad\qquad\qquad|\qquad\backslash\\\qquad\qquad\qquad\qquad\qquad\qquad\qquad\qquad O\qquad O\\\qquad\qquad\qquad\qquad\qquad\qquad\qquad\qquad/\qquad\backslash\\\qquad\qquad\qquad\qquad\qquad\qquad\qquad\qquad C=O\quad C=O\\\qquad\qquad\qquad\qquad\qquad\qquad\qquad\qquad/\qquad\backslash\\\qquad\qquad\qquad\qquad\qquad\qquad\qquad\qquad R^3\qquad R^3\end{array} \quad (1)$$

wherein Ch represents a chelating moiety;
m is 0-3;
$R^1$ is a non-interfering substituent;
l is 0-2;
Z is S or O;
$R^2$ is H or alkyl (1-4C);
n is 0 or 1; and
each $R^3$ is independently an optionally substituted saturated or unsaturated hydrocarbyl group containing at least 10C.

The compounds of formula (1) may also comprise, associated with the chelating agent, at least one paramagnetic metal ion or a radionuclide.

In additional aspects, the invention is directed to compositions comprising lipophilic delivery vehicles associated with the compounds of formula (1) and methods to obtain magnetic resonance or radionuclide images using these compositions. In still other aspects, the invention is directed to methods to prepare the compounds of formula (1) and to methods to prepare the delivery vehicle compositions of the invention.

MODES OF CARRYING OUT THE INVENTION

Figure 1A:
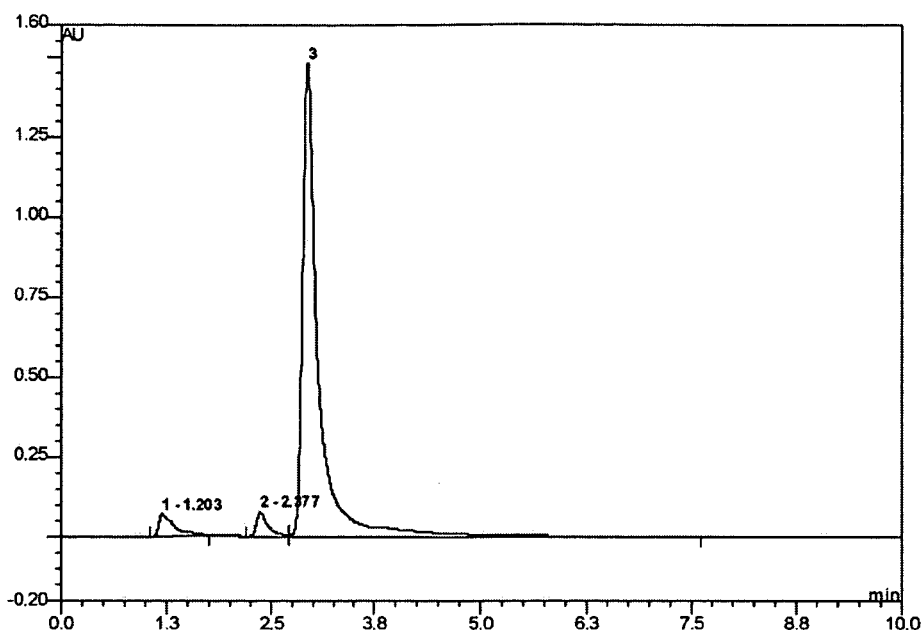
FIGS. 1A and 1B show the results of HPLC on Gd-MeO-DOTA-NCS and Gd-MeO-DOTA-PE, respectively.

In general, the invention is directed to compounds of formula (1), including these compounds which comprise a paramagnetic metal ion or a radionuclide. In one embodiment, the invention does not include compositions or compounds which comprise the specific structure set forth in Example 1.

The compounds of formula (1), when they include an appropriate paramagnetic ion, provide a conveniently prepared MRI contrast agent that has at least two useful features. First, by virtue of its coupling to a phospholipid, it is readily associated with lipophilic delivery vehicles such as liposomes, fluorocarbon nanoparticles, and the like. Second, because it may contain a spacer, the relaxivity of the signal can be controlled by the distance imposed by the spacer from the supporting delivery vehicles. An optional third advantage is that the spacer may provide a cleavage site which permits the contrast agent to be dissociated from the particles and excreted once the image is obtained. The compounds of formula (1) are conveniently prepared from isocyanate or isothiocyanate coupled to the benzene ring associated with the chelating agent. Because of the reactivity of these groups, coupling can be performed to a wide variety of spacers and phospholipids.

The chelating agents represented by Ch typically comprise at least two, and preferably a multiplicity of nitrogens spaced by alkylene groups and to which carboxylic acid-bearing moieties are coupled. Chelating agents are characterized by comprising a multiplicity of unshared electron pairs or potential negative charges which serve to sequester the desired metal ion. Commonly employed chelating agents include porphyrins, ethylenediaminetetraacetic acid (EDTA), diethylenetriamine-N,N,N',N'',N'''-pentaacetate (DTPA), 1,4,10,13-tetraoxa-7,16-diazacyclooctadecane-7 (ODDA), 16-diacetate, N-2-(azol-1(2)-yl)ethyliminodiacetic acids, 1,4,7,10-tetraazacyclododecane-N,N',N'',N'''-tetraacetic acid (DOTA), 1,7,13-triaza-4, 10,16-trioxacyclooctadecane-N,N',N''-triacetate (TTTA), tetraethylene glycols, 1,5,9-triazacyclododecane-N,N',N''-tris(methylenephosphonic acid (DOTRP),N,N',N''-trimethylammonium chloride (DOTMA) and analogues thereof. A particularly preferred chelating agent in the compounds of the invention is DOTA.

The purpose of the chelating agent is, of course, to sequester the desired paramagnetic metals or radionuclides. Suitable paramagnetic metals include a lanthanide element of atomic numbers 58-70 or a transition metal of atomic numbers 21-29, 42 or 44, i.e., for example, scandium, titanium, vanadium, chromium, manganese, iron, cobalt, nickel, copper, molybdenum, ruthenium, cerium, praseodymium, neodymium, promethium, samarium, europium, gadolinium, terbium, dysprosium, holmium, erbium, thulium, and ytterbium, most preferably Gd(III), Mn(II), iron, europium and/or dysprosium. Suitable radionuclides include the radioactive forms of, for example, Sm, Ho, Y, Pm, Gd, La, Lu, Yb, Sc, Pr, Tc, Re, Ru, Rh, Pd, Pt, Cu, Au, Ga, In, Sn, and Pb.

The invention is not limited to compositions of these exemplary radionuclides and paramagnetic ions; however, the foregoing lists are representative.

The phosphoglyceride included in formula (1) is most conveniently derived from naturally occurring lecithins, wherein the groups represented by $R^3COO$ are fatty acids, such as oleic, palmitic, stearic, and the like. However, equally useful in the method of the invention are phosphoglycerides where each $R^3$ is an optionally substituted hydrocarbyl moiety which may be saturated or unsaturated. The hydrocarbyl moiety should contain at least 10C in order to confer sufficient lipophilicity; however, the carbons may be spaced apart by one or two heteroatoms selected from O, N or S. Suitable substituents include substituents that comprise aromatic moieties including heteroatom-containing aromatic moieties, and/or the substituents may be halo, =O, OR, SR, and $NR_2$ wherein each R is independently an optionally substituted alkyl (1-6C). The hydrocarbyl moiety represented by $R^3$ may be branched or straight chain and may comprise one or more cyclic portions. In general, each $R^3$ is simply of sufficient lipophilicity to provide a means for association with the lipophilic particulates or droplets that comprise the carrier. The skilled artisan can readily select embodiments for $R^3$ which fulfill this condition.

The spacer moiety noted in the formula may or may not be present. The spacer may include a portion which has its origin in the phosphoglyceride itself—for example, in one important embodiment, the spacer may be or include the moiety $CH_2CH_2$ derived from a phosphodiglyceride which is a phosphatidyl ethanolamine, wherein the $NR^2$ shown in formula (1) is derived from a phosphatidyl ethanolamine. Preferred embodiments of $R^2$ include methyl, ethyl and H. In some embodiments, the spacer includes portions derived from peptides, pseudopeptides, polyalkylene glycols, such as polyethylene glycol, and the like. (Pseudopeptides are polymers similar to peptides where the peptide linkages have been replaced by isosteric linkages—i.e., wherein CONH linkages are replaced, for example, with $CH_2NH$, CH=CH, and the like.) The length of the spacer may be chosen to control the relaxivity of the signal as described hereinbelow, and further may contain a cleavage site which permits release of the chelate from the carrier particle.

The "non-interfering substituent" $R^1$ on the benzene ring in formula (1) is any substituent, such as alkyl (1-6C), halo, alkoxy (1-6C), and the like, which does not interfere with the coupling of the chelating agent to the remainder of the molecule, or with the ability of the chelating agent to entrap a suitable metal ion, or with the use of the compositions containing the compound of formula (1) in imaging. Methoxy is preferred. It is understood that a variety of substitutions may be present on the benzene ring without interference with the essential features of the compound. Any substituent found to detract significantly from the performance of the compound of formula (1) in chelating metals or in participating in imaging is not included within the scope of the invention. Suitable substituents include OR, $NR_2$, SR, CN, $NO_2$, $SO_3H$, and R where R is alkyl or alkenyl optionally substituted by, e.g., halo, =O, and the like and optionally containing a heteroatom, such as O, S or N.

In general, the compounds of formula (1) are synthesized from a compound of the formula:

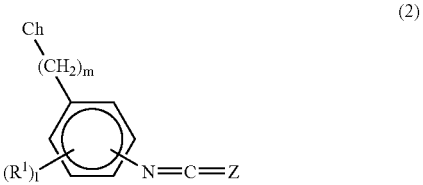

(2)

wherein m, l and $R^1$ are defined as above with a compound of the formula:

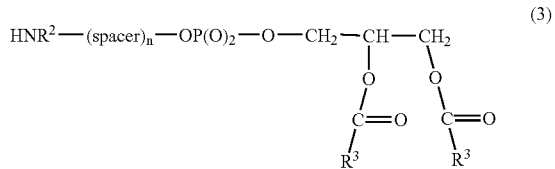

(3)

wherein $R^2$, n and $R^3$ are defined as above. Reactions of this type are facile and conditions for the conduct of such reactions are well known in the art. Typically, the reaction is conducted in an aprotic solvent in the presence of a weak base.

The compounds of formula (1), typically associated with the metal, are included in compositions which contain lipophilic delivery vehicles. "Delivery vehicles" are particulate carriers that are, at least on their surface, lipophilic and which are suspended in a hydrophilic or aqueous medium. These vehicles are microparticles or nanoparticles, and may have average diameters in the range of 10 nm-100 μm, preferably 50 nm-50 μm. However, for in vivo use, particles having diameters in the range of 50-500 nm, preferably 50-300 nm are preferred. The particles may be of a variety of compositions, including such well known vehicles as liposomes, which may be of various sizes and may be unilamellar or multilamellar, micelles, oil droplets, lipoproteins, such as HDL, LDL, IDL, VLDL, chylomicrons, fluorocarbon nanoparticles, microbubbles or nanobubbles, or any of a wide variety of particles in the above mentioned size range that are lipophilic at least at their surface, as further described below. Thus, the surface of these nanoparticles will comprise lipids or surfactants or both.

The compounds of formula (1), when associated with a paramagnetic ion and the lipophilic particles contained in a carrier system are useful in obtaining magnetic resonance images. The vehicles in the delivery system may further comprise other useful components such as targeting agents to carry the contrast agent to the desired tissue or organ and may optionally contain therapeutic or other biologically active agents. In some embodiments, these vehicles may also comprise other imaging agents such as radionuclides, or, more commonly, include the radionuclides, in the alternative, in the chelate.

Targeting agents typically may comprise antibodies or immunospecific fragments thereof, ligands for receptors present on the desired target or tissue, molecules designed specifically to target cellular components such as those designed based on cyclic RGD peptides designed to target integrins and the like. The lipophilic particles themselves may include reactive groups that can be coupled to targeting agents.

Lipid/surfactant components of the delivery vehicles can be coupled to these reactive groups through functionalities contained in the lipid/surfactant component. For example, phosphatidylethanolamine may be coupled through its amino group directly to a desired moiety, or may be coupled to a linker such as a short peptide which may provide carboxyl, amino, or sulfhydryl groups as described below. Alternatively, standard linking agents such a maleimides may be used. A variety of methods may be used to associate the targeting ligand and the ancillary substances to the nanoparticles; these strategies may include the use of spacer groups such as polyethylene glycol or peptides, for example.

For coupling by covalently binding the targeting ligand or other organic moiety to the components of the outer layer, various types of bonds and linking agents may be employed. Typical methods for forming such coupling include formation of amides with the use of carbodiamides, or formation of sulfide linkages through the use of unsaturated components such as maleimide. Other coupling agents include, for example, glutaraldehyde, propanedial or butanedial, 2-iminothiolane hydrochloride, bifunctional N-hydroxysuccinimide esters such as disuccinimidyl suberate, disuccinimidyl tartrate, bis[2-(succinimidooxycarbonyloxy)ethyl]sulfone, heterobifunctional reagents such as N-(5-azido-2-nitrobenzoyloxy)succinimide, succinimidyl 4-(N-maleimidomethyl) cyclohexane-1-carboxylate, and succinimidyl 4-(p-maleimidophenyl)butyrate, homobifunctional reagents such as 1,5-difluoro-2,4-dinitrobenzene, 4,4'-difluoro-3,3'-dinitrodiphenylsulfone, 4,4'-diisothiocyano-2,2'-disulfonic acid stilbene, p-phenylenediisothiocyanate, carbonylbis(L-methionine p-nitrophenyl ester), 4,4'-dithiobisphenylazide, erythritolbiscarbonate and bifunctional imidoesters such as dimethyl adipimidate hydrochloride, dimethyl suberimidate, dimethyl 3,3'-dithiobispropionimidate hydrochloride and the like. Linkage can also be accomplished by acylation, sulfonation, reductive amination, and the like. A multiplicity of ways to couple, covalently, a desired ligand to one or more components of the outer layer is well known in the art. The ligand itself may be included in the surfactant layer if its properties are suitable. For example, if the ligand contains a highly lipophilic portion, it may itself be embedded in the lipid/surfactant coating. Further, if the ligand is capable of direct adsorption to the coating, this too will effect its coupling. For example, nucleic acids, because of their negative charge, adsorb directly to cationic surfactants.

The targeting ligand or antibody may bind directly to the nanoparticle, i.e., the ligand or antibody is associated with the nanoparticle itself, as described above. Alternatively, indirect binding such as that effected through biotin/avidin may be employed. Typically, in biotin/avidin mediated targeting, the ligand or antibody is coupled not to the emulsion, but rather coupled, in biotinylated form, to the targeted tissue.

Ancillary agents that may be coupled to the nanoparticles through entrapment in the coating layer include radionuclides, instead of, or in addition to, the paramagnetic ion. Radionuclides may be either therapeutic or diagnostic; diagnostic imaging using such nuclides is well known and by targeting radionuclides to undesired tissue a therapeutic benefit may be realized as well. Typical diagnostic radionuclides include $^{99m}Tc$, $^{95}Tc$, $^{111}In$, $^{62}Cu$, $^{64}Cu$, $^{67}Ga$, and $^{68}Ga$, and therapeutic nuclides include $^{186}Re$, $^{188}Re$, $^{153}Sm$, $^{166}Ho$, $^{177}Lu$, $^{149}Pm$, $^{90}Y$, $^{212}Bi$, $^{103}Pd$, $^{109}Pd$, $^{159}Gd$, $^{140}La$, $^{198}Au$, $^{199}Au$, $^{169}Yb$, $^{175}Yb$, $^{165}Dy$, $^{166}Dy$, $^{67}Cu$, $^{105}Rh$, $^{111}Ag$, and $^{192}Ir$. The nuclide can be provided to a preformed emulsion in a variety of ways. For example, $^{99}Tc$-pertechnate may be mixed with an excess of stannous chloride and incorporated into the preformed emulsion of nanoparticles. Stannous oxinate can be substituted for stannous chloride. In addition, commercially available kits, such as the HM-PAO (exametazine) kit marketed as Ceretek® by Nycomed Amersham can be used. Means to attach various radioligands to the nanoparticles of the invention are understood in the art. As stated above, the radionuclide may not be an ancillary material, but may instead occupy the chelating agent in lieu of the paramagnetic ion when the composition is to be used solely for diagnostic or therapeutic purposes based on the radionuclide.

Other ancillary agents include fluorophores such as fluorescein, dansyl, quantum dots, and the like.

Included in the lipophilic carrier vehicle as ancillary agents, in some embodiments of the invention, are biologically active agents. These biologically active agents can be of a wide variety, including proteins, nucleic acids, pharmaceuticals, and the like. Thus, included among suitable pharmaceuticals are antineoplastic agents, hormones, analgesics, anesthetics, neuromuscular blockers, antimicrobials or antiparasitic agents, antiviral agents, interferons, antidiabetics, antihistamines, antitussives, anticoagulants, and the like.

In all of the foregoing cases, whether the associated moiety is a targeting ligand for a tissue or organ or is an ancillary agent, the defined moiety may be non-covalently associated with the lipophilic vehicle, may be directly coupled to the components of the vehicle, or may be coupled to said components through spacer moieties.

A multiplicity of vehicles may be used in the compositions of the invention, for example, liposomal particles. The literature describing various types of liposomes is vast and well known to practitioners. As the liposomes themselves are comprised of lipid moieties, the above-described lipids and surfactants are applicable in the description of moieties contained in the liposomes themselves. These lipophilic components can be used to couple to the chelating agent in a manner similar to that described above with respect to the coating on the nanoparticles having an inert core. Micelles are composed of similar materials, and this approach to coupling desired materials, and in particular, the chelating agents applies to them as well. Solid forms of lipids may also be used.

In another example, proteins or other polymers can be used to form the particulate carrier. These materials can form an inert core to which a lipophilic coating is applied, or the chelating agent can be coupled directly to the polymeric material through techniques employed, for example, in binding affinity reagents to particulate solid supports. Thus, for example, particles formed from proteins can be coupled to tether molecules containing carboxylic acid and/or amino groups through dehydration reactions mediated, for example, by carbodiimides. Sulfur-containing proteins can be coupled through maleimide linkages to other organic molecules which contain tethers to which the chelating agent is bound. Depending on the nature of the particulate carrier, the method of coupling so that an offset is obtained between the dentate portion of the chelating agent and the surface of the particle will be apparent to the ordinarily skilled practitioner.

In still another example, PCT publication WO95/03829 describes oil emulsions where the drug is dispersed or solubilized inside an oil droplet and the oil droplet is targeted to a specific location by means of a ligand. U.S. Pat.

No. 5,542,935 describes site-specific drug delivery using gas-filled perfluorocarbon microspheres. The drug delivery is accomplished by permitting the microspheres to home to the target and then effecting their rupture. Low boiling perfluoro compounds are used to form the particles so that the gas bubbles can form.

One important embodiment comprises emulsions wherein the nanoparticles are based on high boiling perfluorocarbon liquids such as those described in U.S. Pat. No. 5,958,371 referenced above. The liquid emulsion contains nanoparticles comprised of relatively high boiling perfluorocarbons surrounded by a coating which is composed of a lipid and/or surfactant. The surrounding coating is able to couple directly to a targeting moiety or can entrap an intermediate component which is covalently coupled to the targeting moiety, optionally through a linker, or may contain a non-specific coupling agent such as biotin. Alternatively, the coating may be cationic so that negatively charged targeting agents such as nucleic acids, in general or aptamers, in particular, can be adsorbed to the surface.

One useful emulsion is a nanoparticulate system containing a high boiling perfluorocarbon as a core and an outer coating that is a lipid/surfactant mixture which provides a vehicle for binding a multiplicity of copies of one or more desired components to the nanoparticle. The construction of the basic particles and the formation of emulsions containing them, regardless of the components bound to the outer surface is described in the above-cited patents to the present applicants, U.S. Pat. Nos. 5,690,907 and 5,780,010; and patents issued on daughter applications 5,989,520 and 5,958,371 and incorporated herein by reference.

The high boiling fluorochemical liquid is such that the boiling point is higher than that of body temperature—i.e., 37° C. Thus, fluorochemical liquids which have boiling points at least 30° C. are preferred, more preferably 37° C., more preferably above 50° C., and most preferably above about 90° C. The "fluorochemical liquids" useful in the invention include straight and branched chain and cyclic perfluorocarbons including perfluorinated compounds which have other functional groups. "Perfluorinated compounds" includes compounds that are not pure perfluorocarbons but rather wherein other halo groups may be present. These include perfluorooctylbromide, and perfluorodichlorooctane, for example.

Useful perfluorocarbon emulsions are disclosed in U.S. Pat. Nos. 4,927,623, 5,077,036, 5,114,703, 5,171,755, 5,304,325, 5,350,571, 5,393,524, and 5,403,575, which are incorporated herein by reference, and include those in which the perfluorocarbon compound is perfluorodecalin, perfluorooctane, perfluorodichlorooctane, perfluoro-n-octyl bromide, perfluoroheptane, perfluorodecane, perfluorocyclohexane, perfluoromorpholine, perfluorotripropylamine, perfluortributylamine, perfluorodimethylcyclohexane, perfluorotrimethylcyclohexane, perfluorodicyclohexyl ether, perfluoro-n-butyltetrahydrofuran, and compounds that are structurally similar to these compounds and are partially or fully halogenated (including at least some fluorine substituents) or partially or fully fluorinated including perfluoroalkylated ether, polyether or crown ether.

It will be noted, that in addition to high boiling halo carbons, the particles useful in the compositions of the invention may contain microbubbles or nanobubbles. Thus, lower boiling components of the particles may be employed such that at temperatures in vivo effect vaporization.

In addition, lipoproteins and chylomicrons may also be used. Various types of lipoprotein are well known and include, for example, LDL, HDL, and VLDL.

In one embodiment, lipid/surfactant coated nanoparticles may be formed by microfluidizing a mixture of a fluorocarbon lipid which forms the core and a lipid/surfactant mixture which forms the outer layer in suspension in aqueous medium to form an emulsion. In this procedure, the lipid/surfactants may already be coupled to additional ligands when they are coated onto the nanoparticles, or may simply contain reactive groups for subsequent coupling. Alternatively, the components to be included in the lipid/surfactant layer may simply be solubilized in the layer by virtue of the solubility characteristics of the ancillary material. Sonication or other techniques may be required to obtain a suspension of the lipid/surfactant in the aqueous medium. Typically, at least one of the materials in the lipid/surfactant outer layer comprises a linker or functional group which is useful to bind an additional desired component or the component may already be coupled to the material at the time the emulsion is prepared.

The lipid/surfactants used to form an outer coating on the delivery vehicles (that will contain the coupled ligand or entrap reagents for binding desired components to the surface) include natural or synthetic phospholipids, fatty acids, cholesterols, lysolipids, sphingomyelins, and the like, including lipid conjugated polyethylene glycol. Various commercial anionic, cationic, and nonionic surfactants can also be employed, including Tweens, Spans, Tritons, and the like. Some surfactants are themselves fluorinated, such as perfluorinated alkanoic acids such as perfluorohexanoic and perfluorooctanoic acids, perfluorinated alkyl sulfonamide, alkylene quaternary ammonium salts and the like. In addition, perfluorinated alcohol phosphate esters can be employed. Cationic lipids included in the outer layer may be advantageous in entrapping ligands such as nucleic acids, in particular aptamers. Typical cationic lipids may include DOTMA, N-[1-(2,3-dioleoyloxy)propyl]-N,N,N-trimethylammonium chloride; DOTAP, 1,2-dioleoyloxy-3-(trimethylammonio)propane; DOTB, 1,2-dioleoyl-3-(4'-trimethylammonio)butanoyl-sn-glycerol,1,2-diacyl-3-trimethylammonium-propane; 1,2-diacyl-3-dimethylammonium-propane; 1,2-diacyl-sn-glycerol-3-ethyl phosphocholine; and 3β-[N',N'-dimethylaminoethane)-carbamol]cholesterol-HCl.

In some embodiments, included in the lipid/surfactant at the surface are components with reactive groups that can be used to couple a targeting ligand or antibody and/or the ancillary substance useful for imaging or therapy.

Use of the Compositions in Magnetic Resonance Imaging

When used in magnetic resonance imaging, the compositions of the invention typically contain a paramagnetic ion within the chelating structure. In such applications, the inclusion of a spacer is particularly advantageous.

As set forth above, the function of the spacer is two-fold: first, by controlling the distance of the chelating agent and thereby the paramagnetic ion from the particles, the exposure of the paramagnetic ion to the hydrogen in the aqueous surroundings of the particles is controlled and thereby the relaxivity of the signal can be adjusted. Second, the spacer may include a cleavable group, thereby expediting the excretion of the chelated metal ion when its imaging function has been served.

Turning first to the effect on relaxivity, to maximize the relaxivities obtainable, the dimensions of the spacer are such that the paramagnetic ion is offset from the surface of the particle at a distance, preferably, of at least 5 or 10 Å. Preferably the average distance at which the paramagnetic ion is found from the surface is between about 5-100 Å, preferably about 10-50 Å, and more preferably about 10-20 Å.

As used herein, the "surface" of the vehicle means the outer limit of the material comprising the particle at the location at which the chelator is coupled. Overall, the mean diameter of the particle itself is compared to the mean distance from the center where the paramagnetic ions reside. This should be at least a 5 Å difference preferably at least 10 Å.

The degree of offset can also be defined in terms of the resultant impact on the relaxivity imparted by the offset. The imparted relaxivity is dependent on the strength of the magnetic field; the relaxivity on a per particle basis is, of course, determined in part by the number of paramagnetic ions associated with the particle itself. At the arbitrarily chosen magnetic field strength of 0.47 T, the offset will be sufficient to enhance the relaxivity on a per ion basis at least 1.2 fold, preferably 1.5 fold, and more preferably 2.5 fold or 10 fold for $\rho_1$ and in similar amounts for $\rho_2$. At the arbitrarily chosen magnetic field of 1.5 T, the offsets will enhance these relaxivities by similar factors. At 4.7 T, preferably the enhancement of $\rho_1$ is at least 1.5 fold, preferably 2 fold and the enhancement of $\rho_2$ is at least two fold and preferably three fold, again, on a per ion basis. In terms of units of relaxivity per se, the offset is such that the value for $\rho_1$ in $(s^*mM)^{-1}$ at 0.47 T is at least 20, and preferably 25, more preferably 30; at 1.5 T, these values would be at least 20, and preferably 30, and at 4.7 T, at least 10, and preferably 14. For $\rho_2$, the corresponding values at 0.47 T would be at least 20, preferably 30, and more preferably 35; at 1.5 T, at least 20, preferably 30; and at 4.7 T, at least 20, more preferably 40, and most preferably 60.

By appropriately coupling the chelating agents, substantial numbers of chelators and paramagnetic ions can be coupled to the particles. For the chelator containing a paramagnetic ion, typically, the particles contain at least 2,000 copies, typically at least 5,000, more typically at least 10,000 or 100,000 or 500,000. For targeting agents, only one or two, or several or more copies may be included. Variable numbers of drug molecules may be contained.

As applicants are able to apply to the vehicles of the composition a multiplicity of chelators containing paramagnetic ions, considerably higher relaxivities can be obtained on a per particle basis. The fold increase in $\rho_1$ and $\rho_2$ on a per particle basis is, of course, similar to that with respect to the fold increase on a per ion basis. Applicants, however, have been able to achieve values of $\rho_1$ in units of $(s^*mM)^{-1}$ on a per particle basis at 0.47 T, of at least $1.8 \times 10^6$, preferably $2.0 \times 10^6$, and more preferably $2.5 \times 10^6$. At 1.5 T, these values are similar and at 4.7 T, relaxivity values for $\rho_1$ are at least $8 \times 10^5$, preferably $1 \times 10^6$, more preferably $1.1 \times 10^6$.

For $\rho_2$ at 0.47 T, the relaxivity is preferably at least $2 \times 10^6$, more preferably $2.5 \times 10^6$, and more preferably $3 \times 10^6$ in these units. At 1.5 T, the values for $\rho_2$ are at least $1.6 \times 10^6$, preferably $2.5 \times 10^6$, and more preferably $3 \times 10^6$. At 4.7 T, $\rho_2$ is at least $3 \times 10^6$, more preferably $4 \times 10^6$, and more preferably $5 \times 10^6$.

The offsetting is accomplished by spacing the dentate portion of the chelate through the spacer to the surface of the vehicle, as the phosphoglyceride associates with the lipophilic material at the surface.

Cleavable Spacers

In a second advantage of use of spacers, the spacer may be cleavable so that the paramagnetic ion or radionuclide ion chelate can be dissociated from the particle or from lipids that compose part of the vehicle. It may be desirable to enhance excretion by liberating the chelate in a hydrophilic status to promote such excretion. Accordingly, the spacer may contain one or more cleavage sites that either are activated externally, for example, by photoactivation, or which are continuously accessed by enzymes present in the cells or bloodstream. Examples of the former include specific linkages that are photoactivated, or cleaved by ultrasound, as is understood in the art. After imaging or therapy has been completed, the nanoparticles are subjected to electromagnetic energy or ultrasound as appropriate to effect cleavage. In the second instance, the spacer may be, or may include, peptides containing amino acid sequences that are susceptible to cleavage by circulating proteases or may include polysaccharides, themselves susceptible to such cleavage. Any combination of such cleavage sites may be included. The susceptibility of the spacer or tether to cleavage thus enhances excretion and diminishes potential toxicity of the paramagnetic ion.

If continuous degradation is employed, the rate may be modulated by selecting spacers according to the available enzymatic activities and by supplying a desired number of cleavage sites. However, it is well known that any peptide circulating in the bloodstream is ultimately destroyed due to circulating proteases; similarly, polysaccharides are subject to cleavage by endogenous enzymes.

Methods of Preparation

The precise process for preparation of the compositions of the invention is variable, and depends on the nature of the particulate vehicle and the choice of spacer molecules, when present. As described above, solid particles which contain reactive groups can be coupled directly to the spacer; lipid-based particles such as oil emulsions, solid lipids, liposomes, fluorocarbon nanoparticles and the like, can include lipophilic materials containing reactive groups which may covalently, then, be coupled to linking moieties which bear the dentate portion of the chelating agent. In one particularly preferred embodiment, the process involves mixing a liquid fluorocarbon compound that forms the core of a nanoparticle and the components of a lipid/surfactant coating for that particle in an aqueous suspension, microfluidizing, and, if desired, harvesting and sizing the particles. The components to be coupled can be included in the original mixture by virtue of their initial coupling to one or more components of the lipid/surfactant coating, or the coupling to additional moieties can be conducted after the particles are formed.

Kits

The emulsions of the invention may be prepared and used directly in the methods of the invention, or the components of the emulsions may be supplied in the form of kits. The kits may comprise the pre-prepared targeted composition containing all of the desired ancillary materials in buffer or in lyophilized form. Alternatively, the kits may include a form of the emulsion which lacks the compound of formula (1) and/or a targeting agent which is supplied separately. If the targeting agent is to be directly bound, the emulsion will contain a reactive group, such as a maleimide group, which, when the emulsion is mixed with the targeting agent, effects the binding of the targeting agent to the emulsion itself. A separate container may also provide additional reagents useful in effecting the coupling. Alternatively, the emulsion may contain reactive groups which bind to linkers coupled to the desired component to be supplied separately which itself contains a reactive group. A wide variety of approaches to constructing an appropriate kit may be envisioned. Individual components which make up the ultimate emulsion may thus be supplied in separate containers, or the kit may simply contain reagents for combination with other materials which are provided separately from the kit itself.

A non-exhaustive list of combinations might include: emulsion preparations that contain, in their lipid-surfactant layer, an ancillary component such as a fluorophore or chelating agent and reactive moieties for coupling to the targeting agent; the converse where the emulsion is coupled to targeting agent and contains reactive groups for coupling to an ancillary material; emulsions which contain both targeting agent and a chelating agent but wherein the metal to be chelated is either supplied in the kit or independently provided by the user; preparations of the nanoparticles comprising the surfactant/lipid layer where the materials in the lipid layer contain different reactive groups, one set of reactive groups for a targeting agent and another set of reactive groups for an ancillary agent; preparation of emulsions containing any of the foregoing combinations where the reactive groups are supplied by a linking agent.

Applications

The emulsions and kits for their preparation are useful in the methods of the invention which include imaging of tissues and providing therapeutic agents.

The magnetic resonance imaging contrast agents of the present invention may be used in a similar manner as other MRI agents as described in U.S. Pat. No. 5,155,215; U.S. Pat. No. 5,087,440; Margerstadt, et al., *Magn. Reson. Med.* (1986) 3:808; Runge, et al., *Radiology* (1988) 166:835; and Bousquet, et al., *Radiology* (1988) 166:693. Other agents that may be employed are those set forth in U.S. patent publication 2002/0127182 which are pH sensitive and can change the contrast properties dependent on pulse. Generally, sterile aqueous solutions of the contrast agents are administered to a patient intravenously in dosages ranging from 0.01 to 1.0 mmoles per kg body weight.

Usually, the diagnostic compositions for radionuclide imaging are administered by intravenous injection, usually in saline solution, at a dose of 1 to 100 mCi per 70 kg body weight, or preferably at a dose of 5 to 50 mCi. Imaging is performed using known procedures.

The therapeutic radiopharmaceuticals are administered by intravenous injection, usually in saline solution, at a dose of 0.01 to 5 mCi per kg body weight, or preferably at a dose of 0.1 to 4 mCi per kg body weight. For comparable, i.e., analogous therapeutic radiopharmaceuticals, current clinical practice sets dosage ranges from 0.3 to 0.4 mCi/kg for Zevalin™ to 1-2 mCi/kg for OctreoTher™, a labeled somatostatin peptide. For such therapeutic radiopharmaceuticals, there is a balance between tumor cell kill vs. normal organ toxicity, especially radiation nephritis. At these levels, the balance generally favors the tumor cell effect. These dosages are higher than corresponding imaging isotopes.

When the compositions of the invention contain targeted delivery vehicles, suitable targets include any tissue of interest, including tumor tissue, atherosclerotic plaques, blood clots, and the like. The choice of targeting agent will, of course, depend on the nature of the target itself. For example, to target atherosclerotic plaques or blood clots, antifibrin antibodies are appropriate as are peptidomimetics that interact with $\alpha_v\beta_3$ receptors. Suitable targeting agents for tumors may include antibodies prepared against tumor associated antigens or prepared with respect to the organ hosting the tumor. Imaging of particular organs would employ targeting agents that interact with receptors or other characteristic moieties associated with the target itself.

The following examples are intended to illustrate but not to limit the invention.

Preparation A

Nanoparticle Preparation

Paramagnetic nanoparticles were produced in a modification of the procedure described by Lanza, G, et al., *Circulation* (1996) 94:3334-3340. Briefly, the emulsions comprised 40% (v/v) perfluorooctylbromide (PFOB; MMM, St. Paul, Minn.), 2% (w/v) safflower oil, 2% (w/v) of a surfactant co-mixture, 1.7% (w/v) glycerin and water representing the balance. The surfactant co-mixture included 63 mole % lecithin (Avanti Polar Lipids, Inc., Alabaster, Ala.), 15 mole % cholesterol (Sigma Chemical Co., St. Louis, Mo.), 2 mole % dipalmitoyl-phosphatidylethanolamine (Avanti Polar Lipids, Inc., Alabaster, Ala.), and 20 mole % of the paramagnetic lipophilic chelate. The lipophilic chelate was either gadolinium diethylene-triamine-pentaacetic acid-bis-oleate (Gd-DTPA-BOA; Gateway Chemical Technologies, St. Louis, Mo.) or DTPA-phosphatidylethanolamine (DTPA-PE; Gateway Chemical Technologies, St. Louis, Mo.). The surfactant components were dissolved in chloroform, evaporated under reduced pressure, dried in a 50° C. vacuum oven overnight and dispersed into water by sonication. The suspension was pre-emulsified in a blender with PFOB, safflower oil and distilled deionized water for 30 to 60 seconds and then emulsified in a M110S Microfluidics emulsifier (Microfluidics, Newton, Mass.) at 20,000 PSI for four minutes. The completed formulation was placed in crimp sealed vials and blanketed with nitrogen. Particle sizes were determined in triplicate at 37° C. with a laser light scattering submicron particle sizer (Malvern Instruments, Malvern, Worcestershire, UK).

EXAMPLE 1

Preparation of a Compound of Formula (1)

Phosphoethanolamine diglyceride (PE) is first coupled to t-boc protected triglycine. Standard coupling techniques, such as forming the activated ester of the free acid of the t-boc-triglycine using diisopropyl carbodiimide (or an equivalent thereof) with either N-hydroxy succinimide (NHS) or hydroxybenzotriazole (HBT) are employed and the t-boc-triglycine-PE is purified.

Treatment of the t-boc-triglycine-PE with trifluoroacetic acid yields triglycine-PE, which is then reacted with excess DOTA-NCS in DMF/CHCl$_3$ at 50° C. for 8 hours. The final product is isolated by removing the solvent, followed by rinsing the remaining solid with excess water, to remove excess solvent and any un-reacted or hydrolyzed DOTA-NCS.

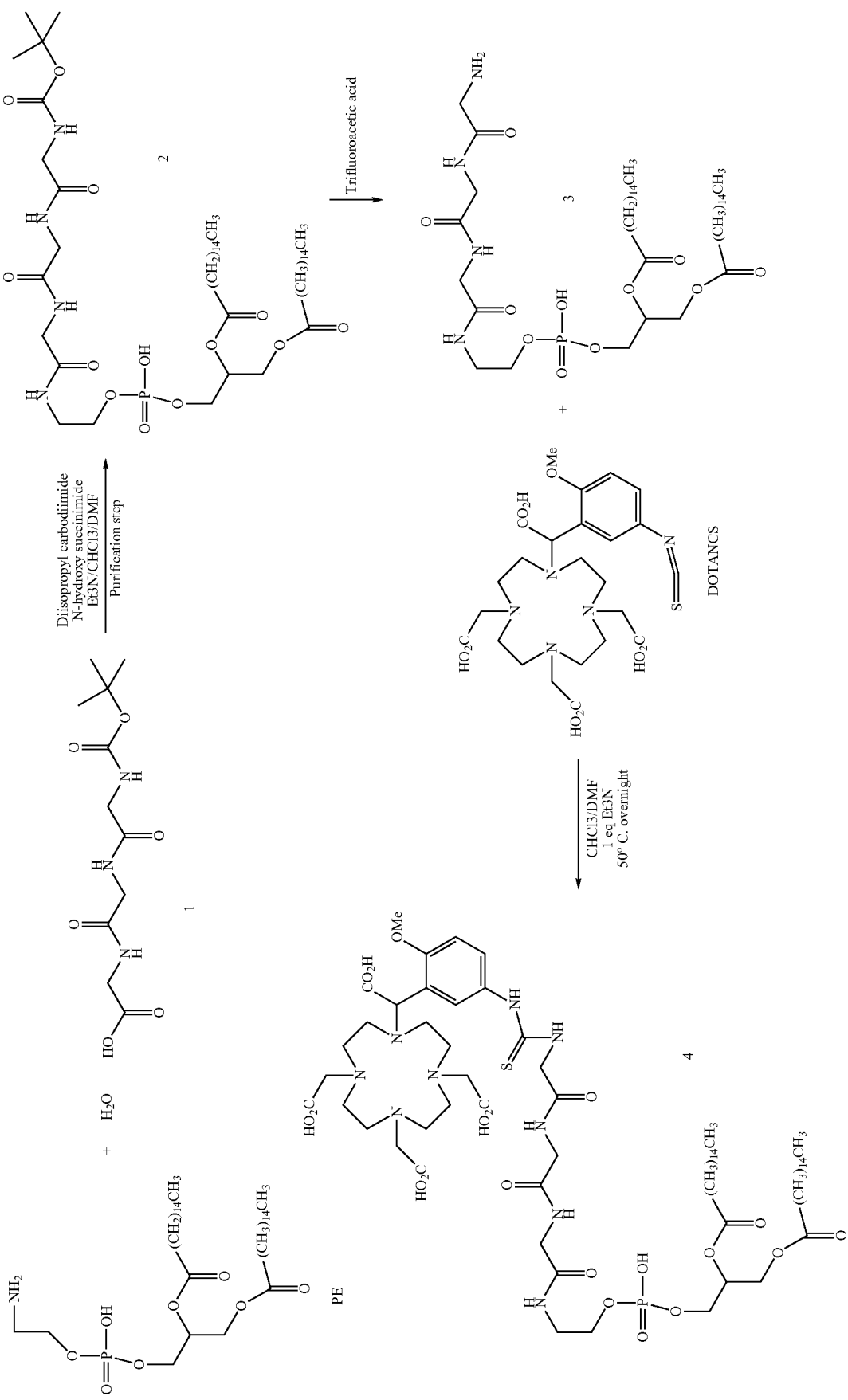

It will be noted that the triglycine spacer is a cleavable linker as a substrate for proteases. Alternatively, instead of the triglycine spacer, a similar construct was prepared using caproylamine-PE, which is commercially available from Avanti Polar Lipids. This material is reacted with DOTA-NCS in an analogous manner to that set forth with respect to the glycine spacer described above.

EXAMPLE 2

Introduction of Gadolinium Ion

Gadolinium ion may be introduced into the chelate either by initially metalating DOTA-NCS or metalating the compound of formula (1) after synthesis.

Premetalation of MeO-DOTA-NCS was carried out in aqueous $GdCl_3$. The reaction mixture was lyophilized to dryness and used without further purification prior to conjugation with PE or triglycyl-PE. As the salts carried onto the final conjugation negatively affect the coupling chemistry, they were removed by aqueous rinses of the dried MeODOTA-Gd-PE reaction mixture.

$Gd_2O_3$ may be used in place of $GdCl_3$ to produce a "salt free" metal complex, by boiling the solution containing $Gd_2O_3$ for an extended period of time in MeOH/chloroform.

Postmetalation of conjugated MeO-DOTA-PE is carried out with $GdCl_3$ in a chloroform methanol mixture with boiling.

Gd-MeO-DOTA was characterized by HPLC. LC conditions were: Zorbax CB C8 column, 25% acetonitrile, 0.2% TFA isocratic elution, detection at 260 nm. Uncomplexed MeO-DOTA-NCS elutes at 3.8-4.0 min. MeO-DOTA-PE was characterized by LC and MS. The HPLC conditions for the characterization of Gd-MeODOTA-PE were: Astec, Pholipidec column; solvent system: solvent A (80% CHCl3, 19% MeOH, 1% NH4OH) and solvent B (MeOH), gradient profile: 0-10 min 100-75% A, 0-25% B; 10-15 min 25-100% B, hold at 100% B from 15-20 min, 100-0% B from 20-22 min, hold at 100% for 5 min. ELSD and UV detectors were employed.

Figure 1B:
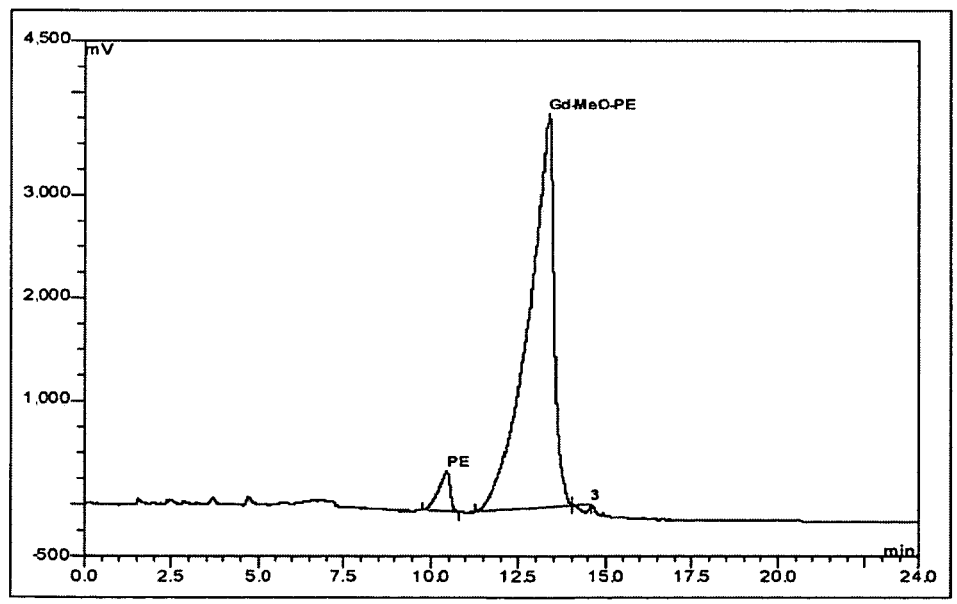
Figure 2:
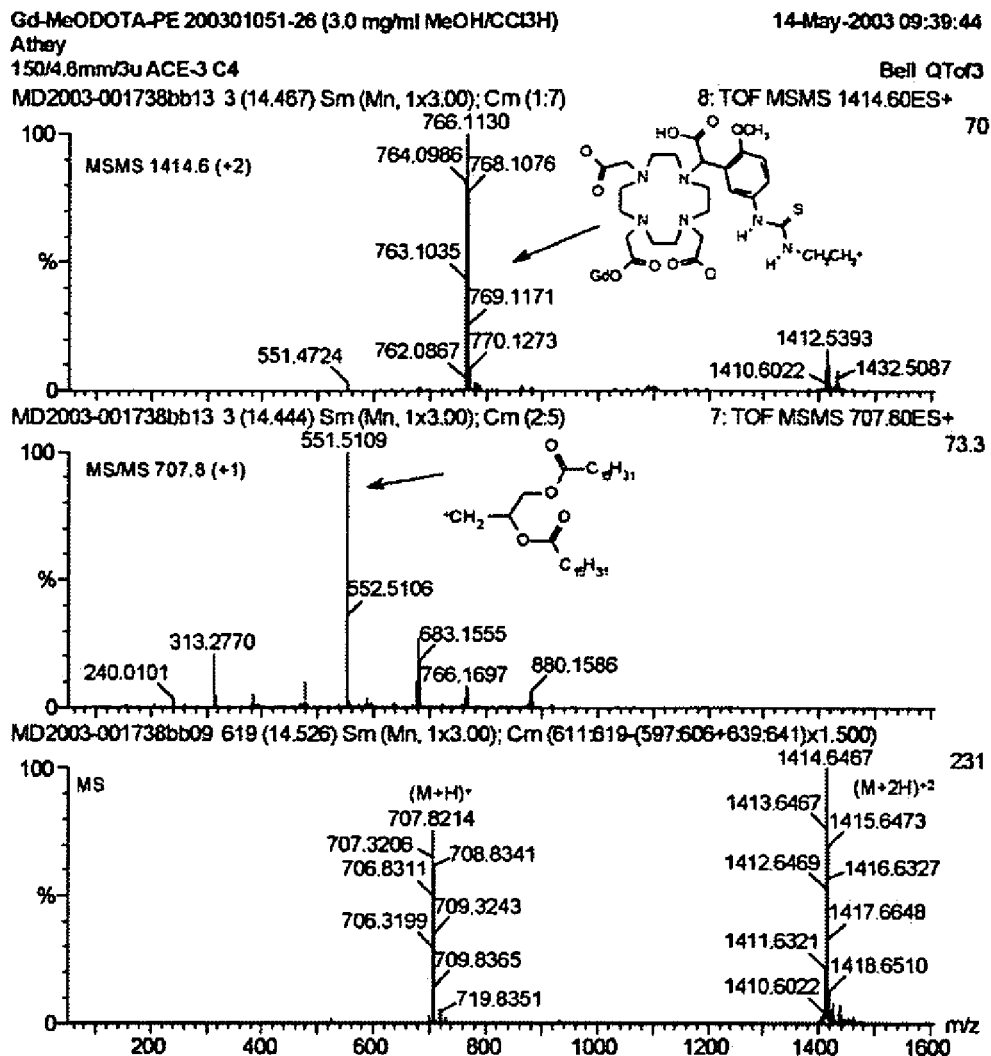
FIG. 2 shows the mass spectrum for Gd-MeO-DOTA-PE.

The HPLC results for Gd-MeO-DOTA-NCS and for the corresponding conjugate Gd-MeO-DOT-PE are shown in FIGS. 1A and 1B, respectively. The mass spectrum of the resulting Gd-MeO-DOTA-PE is shown in FIG. 2.

EXAMPLE 3

Synthesis of Conjugate for Animal Studies

A. Preparation of GdMeODOTA-NCS

MeO-DOTA-NCS (Dow Chemical) (18.71 g, 33 mmol) was dissolved in deionized water (500 mL). A pH probe was placed into the solution and while being stirred, the pH of the solution was adjusted to 6 with the addition of NaOH (50%). In a separate flask, $GdCl_3 \cdot 6H_2O$ (Ohduch) (18.37 g) was dissolved in 100 mL of DI water. The Gd solution was carefully added to the stirring solution of 3 in 5 mL aliquots. After each addition, the pH was measured and adjusted PRN to a pH of 6-7 with the addition of sodium hydroxide (50%). The solution was lyophilized to dryness. This process produced 43.9 g of a faintly, green powder with an overall purity of 92%.

B. Preparation of Gd-MeO-DOTA-PE

A 2 L, 3-neck round-bottom flask was charged with Gd-MeO-DOTA-NCS prepared in paragraph A. (43.9 g, mmol); PE (15 g, 22 mmol); DMF (500 mL); Et3N (4.57 mL); and $CHCl_3$ (300 mL). PE was supplied as 1,2-dipalmitoyl-sn-glycerol-3-phosphoethanolamine obtained from Avanti. The mixture was heated for 8 hours at 50° C. The reaction was monitored by HPLC. The solvents were removed in vacuo, and the resulting solid was suspended in water (~100 mL), then filtered over a bed of Celpure filtering agent (8-10 cm thick), using a coarse fritted funnel. The solids were rinsed with copious amount of water (1 L-1.5 L). After the majority of the water had been removed from the solid cake layer, the solids were rinsed with $CHCl_3$:MeOH (3:1) (total volume of ~1 L-1.5 L). The organic filtrate solution was dried over sodium sulfate. The mixture was filtered and dried in vacuo, leaving 20 g of light beige, glassy, solid. The overall purity was 90% based on LC.

Figure 3:
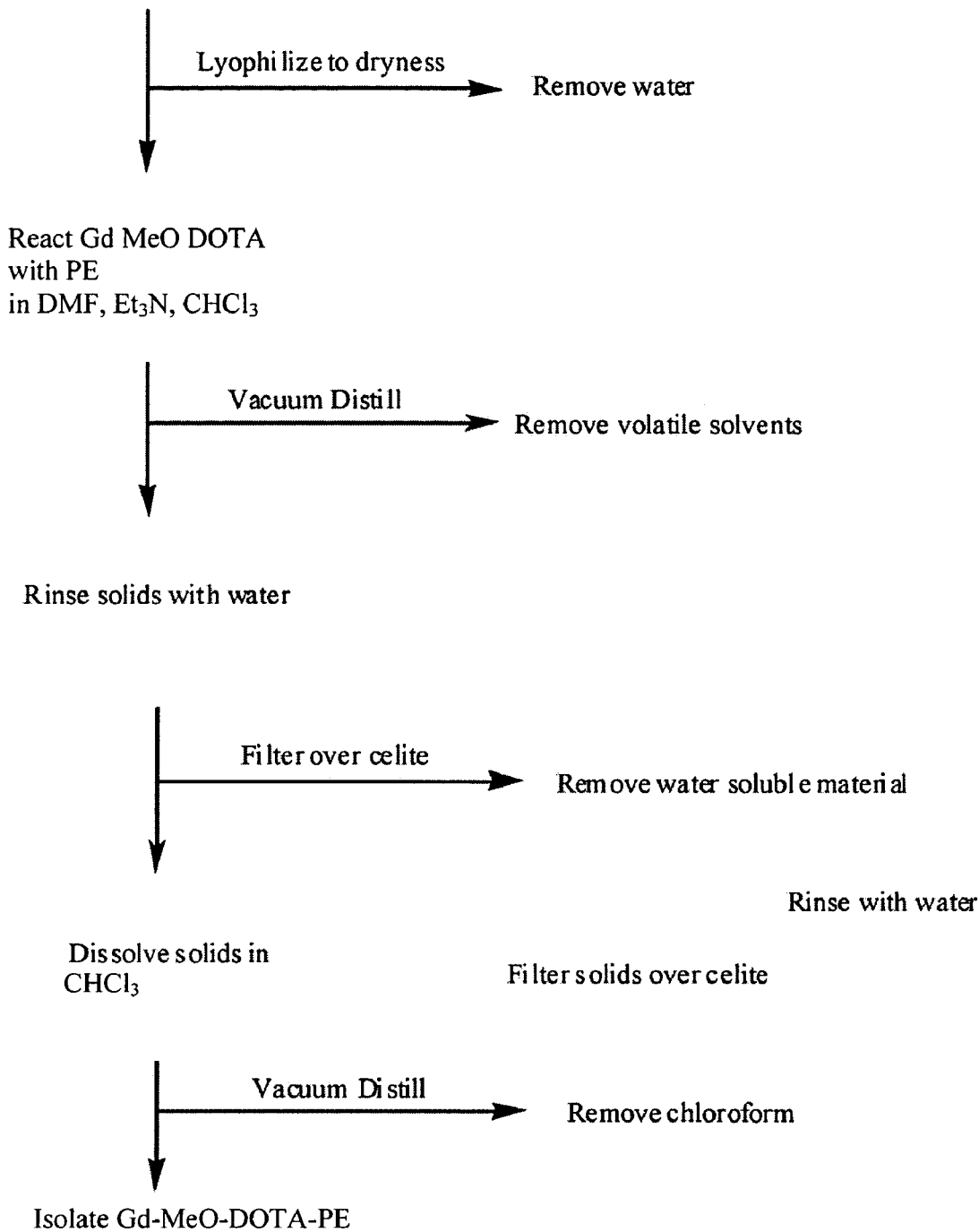
FIG. 3 shows a process flow chart for the preparation of Gd-MeO-DOTA-PE.

A process flow chart for the preparation of the final product is shown in FIG. 3.

EXAMPLE 4

Effect of Spacer Length on Relaxivity

In this example, an embodiment of the invention employing DTPA as the chelator (Ch), gadolinium as the paramagnetic ion, ultimately linked to phosphatidyl ethanolamine was used to indicate the effect of spacer length on relaxivity. Although the Gd-DTPA-PE itself does not fall within the scope of the compounds of the invention, the data in this example illustrate the effect of the spacing of the chelating agent from the particles in the composition on relaxivity. DTPA-PE can be purchased from Gateway Chemical Technologies, St. Louis, Mo. It was compared with the relaxivity generated by gadolinium diethylenetriaminepentaacetic acid-bisoleate (Gd-DTPA-BOA) which can also be purchased from Gateway.

The nanoparticles were prepared as described in Preparation A and the chelates purchased from Gateway incorporated as there described. Gadolinium chloride was added in excess proportions as opposed to emulsification step to the nanoparticles formulated with DTPA-PE. Unbound gadolinium was removed by dialysis against distilled deionized water (300,000 mw cutoff, Spectrum Laboratories, Rancho Dominguez, Calif.). Gd-DTPA-BOA had been incorporated as the complete compound as described. Both compositions were tested for free $Gd^{3+}$ using the arsenazo III reaction and showed no sign of unbound gadolinium.

The Gd-DTPA-BOA and Gd-DTPA-PE nanoparticles had the following characteristics:

TABLE 1

Properties of Paramagnetic Nanoparticles.

|  | Gd-DTPA-BOA | Gd-DTPA-PE |
|---|---|---|
| Particle Size (nm) | 287 | 261 |
| Polydispersity Index | 0.28 | 0.23 |
| [$Gd^{3+}$] (mM) | 3.36 | 5.79 |
| $Gd^{3+}$ Ions/Particle | 56,900 | 73,600 |
| [Particles] (nM) | 59.1 | 78.7 |

The particles were diluted to 0, 4, 6, 8, 10 and 12% PFOB (v/v) with distilled deionized water. The initial nanoparticle formulation contained 26.1 mol/L $^{19}F$ and the diluted aliquots had 0, 3.915, 5.22, 6.525 and 7.83 mol/L $^{19}F$, respectively. Total gadolinium content was determined by neutron activation analysis. The gadolinium contents of the Gd-DTPA-BOA nanoparticle dilutions were 0; 0.336; 0.504; 0.672; 0.84; and 1.01 mmol/L $Gd^{3+}$. The paramagnetic ion concentrations in Gd-DTPA-PE samples were 0; 0.579; 0.869; 1.16; 1.45; and 1.74 mmol/L $Gd^{3+}$.

The proton longitudinal and transverse relaxation rates ($1/T_1$ and $1/T_2$, respectively) of each sample were measured at 40° C. on a Bruker MQ20 Minispec NMR Analyzer with a field strength of 0.47 T. $T_1$ was measured using an inversion recovery sequence with 10 inversion delay values, while $T_2$ was measured with a Carr-Purcell-Meiboom-Gill (CPMG) sequence. The $T_1$ and $T_2$ relaxivities (i.e., $\rho_1$ and $\rho_2$, respectively) were calculated from the slope of the linear least-squares regression of longitudinal and transverse relaxation rates versus $Gd^{3+}$ (i.e., ion relaxivity) or nanoparticle (i.e., particle relaxivity) concentrations and are reported in units of $(s*mM)^{-1}$.

Spin echo images from a clinical scanner (Gyroscan NT, PowerTrak 6000, Philips Medical Systems, Best, Netherlands) obtained with a standard 11 cm diameter surface coil were used to measure the relaxivity of the two nanoparticle formulations at 1.5 T. A six chamber phantom allowed all six dilutions to be studied in parallel. To accommodate the different relaxation times of the two paramagnetic formulations, different imaging parameters were applied. $T_1$ was calculated from an inversion recovery MRI pulse sequence. The measurement for the Gd-DTPA-BOA phantom included six inversion times ($T_1$) ranging from 50 to 1500 ms, while the Gd-DTPA-PE value utilized seven $T_1$ values ranging from 5 ms to 200 ms. The signal intensity (S1) from each chamber was fit to the equation:

$$S1_{T1} = S1_0 * (1-EXP(-T1/T_1)), \quad [1]$$

where $S1_0$ represents the equilibrium signal intensity. The $T_2$ value for Gd-DTPA-BOA was derived from a multi-echo sequence with 8 echo times (TE) ranging from 20 ms to 160 ms. Nine separate images with echo times ranging from 4.5 ms to 200 ms were used to calculate the $T_2$ relaxation for the Gd-DTPA-PE phantom. MRI signal intensity was fit to the equation:

$$S1_{TE} = S1_0 * EXP(-TE/T_2). \quad [2]$$

The imaging parameters common for both formulations were: TR=1000 ms, TE=5 ms (unless otherwise noted), number of signal averages=4, image matrix=128 by 128, FOV=7 cm by 7 cm, flip angle=90°, slice thickness=5 mm.

The relaxivities of the two paramagnetic formulations were also measured with a 4.7 T magnet interfaced to a Varian INOVA console (Varian Associates, Palo Alto, Calif.) using a 5 cm birdcage coil. As stated earlier, a six chamber phantom was used to study the various emulsion dilutions concurrently. $T_1$ and $T_2$ values were obtained with inversion recovery (TE=7.2 ms, $T_1$ varied from 1 to 800 ms) and spin echo (TE varied from 7.2 to 100 ms) pulse sequences, respectively. The images were collected with TR=3000 ms, number of signal averages=4, image matrix=256 by 256, FOV=4 cm by 4 cm, flip angle=90°, slice thickness=2 mm.

Finally, the relaxivities of the two paramagnetic preparations were measured independently at magnetic fields ranging from 0.05 T to 1.3 T (2-56 MHz) using a custom built variable field relaxometer (Southwest Research Institute, San Antonio, Tex.). The samples were measured at temperatures of 3° and 37° C. A saturation recovery pulse sequence with 32 incremental τ values was used to measure $\rho_1$, while $\rho_2$ was measured using a CPMG pulse sequence with 500 echoes and a 2 ms inter-echo delay time.

Table 2 shows $T_1$ and $T_2$ relaxivities of the Gd-DTPA-BOA and Gd-DTPA-PE paramagnetic formulations determined at three magnetic field strengths.

TABLE 2

Relaxivities of Gd-DTPA-BOA and Gd-DTPA-PE emulsions at three different field strengths

| Magnetic Field | Paramagnetic Chelate | Ion-Based Relaxivity $(s*mM)^{-1}$ | | Particle-Based Relaxivity $(s*MM)^{-1}$ | |
|---|---|---|---|---|---|
| | | $\rho_1$ | $\rho_2$ | $\rho_1$ | $\rho_2$ |
| 0.47 T | Gd-DTPA-BOA | 21.3 ± 0.2 | 23.8 ± 0.3 | 1,210,000 ± 10,000 | 1,350,000 ± 20,000 |
| | Gd-DTPA-PE | 36.9 ± 0.5 | 42.3 ± 0.6 | 2,710,000 ± 40,000 | 3,110,000 ± 50,000 |
| 1.5 T | Gd-DTPA-BOA | 17.7 ± 0.2 | 25.3 ± 0.6 | 1,010,000 ± 10,000 | 1,440,000 ± 30,000 |
| | Gd-DTPA-PE | 33.7 ± 0.7 | 50 ± 2 | 2,480,000 ± 50,000 | 3,700,000 ± 100,000 |
| 4.7 T | Gd-DTPA-BOA | 9.7 ± 0.2 | 29.4 ± 0.3 | 549,000 ± 9,000 | 1,670,000 ± 20,000 |
| | Gd-DTPA-PE | 15.9 ± 0.1 | 80 ± 0.7 | 1,170,000 ± 6,000 | 5,880,000 ± 50,000 |

At all magnetic field strengths, both the ion-based and particle-based $\rho_1$ of the Gd-DTPA-PE formulation were about two-fold greater (p<0.05) than $\rho_1$ of the Gd-DTPA-BOA agent. Similarly, ion-based and particle-based $\rho_2$ of the Gd-DTPA-PE agent were approximately two-fold higher (p<0.05) than $\rho_2$ of the Gd-DTPA-BOA system at the lowest magnetic field strength (0.47 T), and this relative difference was more than three-fold greater (p<0.05) at the highest field strength (4.7 T).

At 1.5 T, a typical medical imaging field strength, the ion-based $\rho_1$ and $\rho_2$ for Gd-DTPA-BOA were 17.7±0.2 $(s*mM)^{-1}$ (mean±standard error) and 25.3±0.6 $(s*mM)^{-1}$, respectively, consistent with our previous reported estimates (Flacke, S., et al., Circulation (2001) 104:1280-1285). Incorporation of Gd-DTPA-PE (as opposed to Gd-DTPA-BOA) increased the ion-based $\rho_1$ and $\rho_2$ to 33.7±0.7 $(s*mM)^{-1}$ and 50.0±2 $(s*mM)^{-1}$, respectively. More importantly from a targeted agent perspective, the particle-based $\rho_1$ and $\rho_2$ for Gd-DTPA-BOA were 1,010,000±10,000 $(s*mM)^{-1}$ and 1,440,000±30,000 $(s*mM)^{-1}$, respectively, and for Gd-DTPA-PE nanoparticles the particle-based $\rho_1$ and $\rho_2$ were 2,480,000±50,000 $(s*mM)^{-1}$ and 3,700,000±100,000 $(s*mM)^{-1}$, respectively. To our knowledge, particulate or molecular relaxivities in these ranges are the highest values reported to date for any targeted or blood pool paramagnetic contrast agent at these field strengths.

Magnetic field strength influences relaxivity. The magnitudes of ion and particle longitudinal relaxivities decline as magnetic field strength increased from 0.47 T to 4.7 T, whereas the ion and particle transverse relaxivities progressively increased with higher field strengths. Although the particle longitudinal relaxivity declined about 50% at 4.7 T compared to 1.5 T, the particle $\rho_1$ remained very high. As a ligand-targeted contrast agent, the decreases in relaxivity at higher field strengths will be effectively offset by reduced voxel sizes, smaller partial volume dilution effects and improved signal to noise.

Variable field relaxometry measurements show that $\rho_1$ of both emulsions was dominated by the long correlation time ($\tau_c$) of the slowly tumbling emulsion complex (FIG. 3). In fact, the particles were relatively so large, that there was almost no field dependence (dispersion). In contrast, the $\rho_2$ values initially followed those of $\rho_1$ but did not decrease at higher fields in accordance with expectations based on the Solomon-Bloembergen equations (Wood, M. L., *J. Mag. Res. Imag.* (1993) 3:149-156) (due to the non-dispersive term involving $\tau_c$). For the Gd-DTPA-BOA emulsion, the "peak" $\rho_1$ relaxivity was around 25 $(s*mM)^{-1}$ and the maximum value of $\rho_2$ was 30 $(s*mM)^{-1}$. The value of $\rho_1$ was largely independent of temperature, but $\rho_2$ increased at the lower temperature. For the Gd-DTPA-PE emulsion, however, the relaxivities were much higher, with $\rho_1$ reaching 40 $(s*mM)^{-1}$ at 40 MHz (approx. 1.7 T) and $\rho_2$ reaching 50 $(s*mM)^{-1}$ at 56 MHz (1.3 T). The temperature dependence of Gd-DTPA-PE was also different from Gd-DTPA-BOA with $\rho_1$ decreasing at the lower temperature and $\rho_2$ remaining independent of temperature. The relaxometry values were consistent with analogous measurements made at 0.47 T and 1.5 T (Table 2). Moreover, the temperature dependence of these curves suggested that the Gd-DTPA-PE chelate has better access to water (i.e., faster exchange) compared to Gd-DTPA-BOA.

EXAMPLE 5

Enhanced Relaxivity of Contrast Agent Coupled to Nanoparticles

Figure 4:
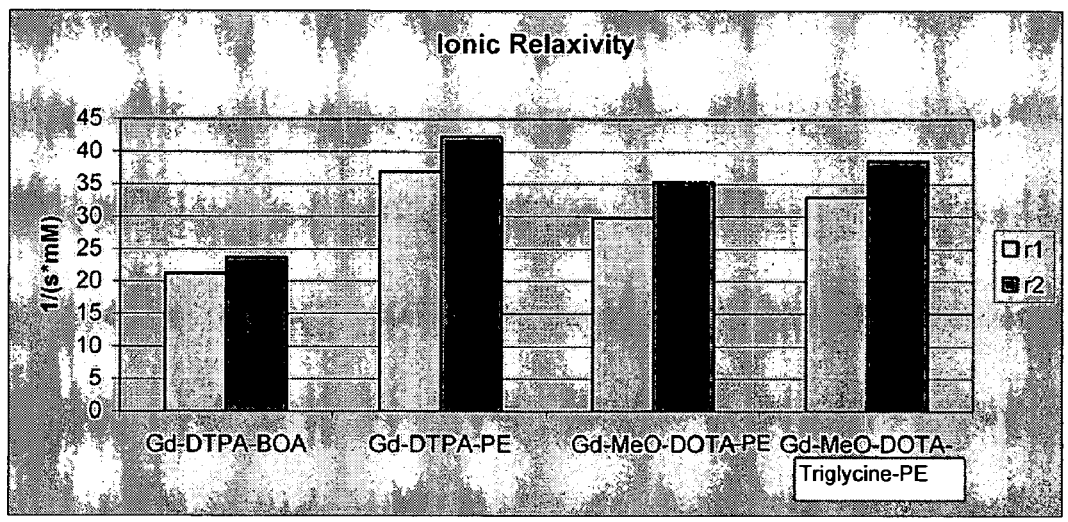
FIG. 4 shows the $\rho_1$ (relaxivity) value for various particulate chelate preparations on a per ion basis.
Figure 5:
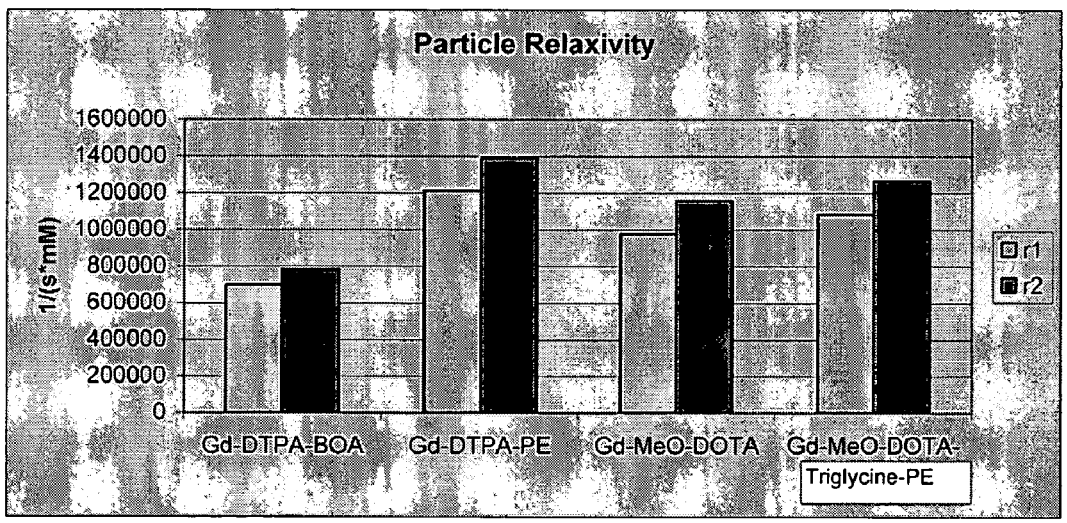
FIG. 5 shows the $\rho_1$ relaxivity values for these particulate chelates on a per particle basis.

The Gd-MeO-DOTA-PE and Gd-MeO-DOTA-triglycine-PE conjugates were associated with nanoparticles prepared as in Preparation A and associated with the nanoparticles as described in that Preparation. Each particle contains approximately 33,000 $Gd^{3+}$ chelates. The $\rho_1$ relaxivity was compared, as described in Example 4, with the relaxivities obtained from similar nanoparticles coupled with similar amounts of Gd-DTPA-BOA and Gd-DTPA-PE. The results are shown on a per ion basis and per particle basis in FIGS. 4 and 5, respectively.

The $\rho_1$ value on a per ion basis for Gd-DTPA-BOA nanoparticles was 21.3 $s*mM^{-1}$; that of Gd-MeO-DOTA-PE nanoparticles is 29.8 $s*mM^{-1}$, and of Gd-MeO-DOTA-triglycine-PE nanoparticles is 33.0 $s*mM^{-1}$. Since each particle carries 33,000 $Gd^{3+}$-chelates, the particulate relaxivities were Gd-DTPA-BOA: 700,000 $s*mM^{-1}$, Gd-MeO-DOTA-PE: 980,000 $s*mM^{-1}$ and Gd-MeO-DOTA-Triglycine-PE: 1,100,000 $s*mM^{-1}$. It is seen that the triglycine spacer improves relaxivity, and that the relaxivity for both conjugates using DOTA and PE spacer are improved over that of Gd-DTPA-BOA.

EXAMPLE 6

Transmetalation

As described above, the coupled nanoparticles may be coupled to a targeting agent which will delay clearance from the subject as compared to non-targeted chelating agents such as blood pool contrast agents. This makes retention of metal by the chelate of significance; retention of metal by macrocyclic chelates, such as DOTA is known to be orders of magnitude stronger than for linear chelates such as DTPA or EDTA. Further, use of a coupling site not a part of the chelator itself results in efficient coupling without sacrificing chelation strength.

An excess of zinc was used as a competing species to produce transmetalation in GD-DTPA-BOA nanoparticles and nanoparticles coupled to the invention conjugates. The longitudinal relaxation of Gd-DTPA-BOA nanoparticles decreased quickly after addition of $ZnCl_2$, whereas neither DOTA chelate showed a high rate or high magnitude of change in relaxivity, reflecting the improved stability of the invention $Gd^{3+}$ complexes. The retained gadolinium at equilibrium was much higher for the two DOTA chelates (91%) compared to the DTPA chelate (75%). Thus, the DOTA chelates demonstrated 40-55% higher relaxivity and 64% lower transmetalation than the linear Gd-DTPA-BOA chelate.

EXAMPLE 7

Effect of Cleavable Linker on Clearance

Figure 6A:
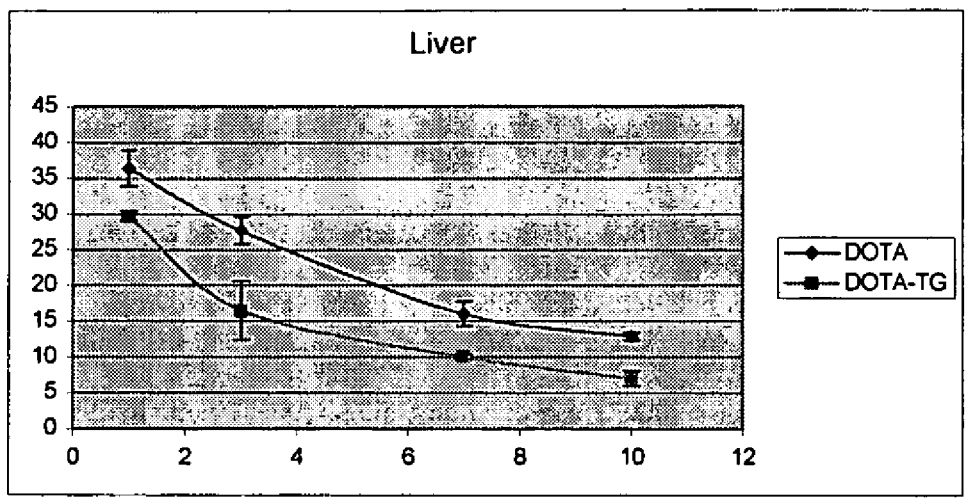
FIGS. 6A and 6B show the percent gadolinium retained in liver and spleen, respectively, in animals administered particulate chelates with and without cleavable triglycine linker.
Figure 6B:
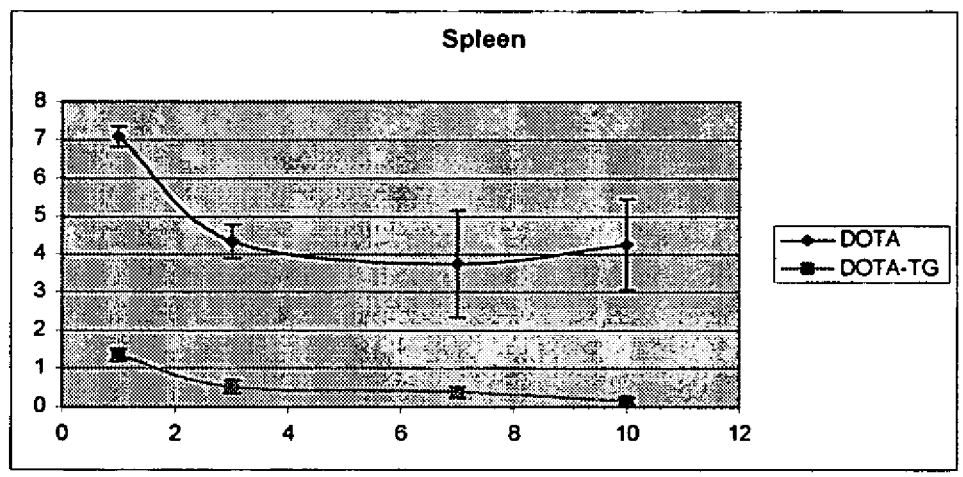

Gd-MeO-DOTA-PE and Gd-MeO-DOTA-triglycine-PE nanoparticles were administered intravenously to Sprague Dawley rats at standard dosages, i.e., 0.5 ml/kg of 40 wt % perfluorocarbon emulsion. Livers and spleens were obtained from each animal (n=3 per treatment) at each time point and analyzed for gadolinium. The results are shown as percent of injected dose retained per organ in FIGS. 6A (liver) and 6B (spleen). As shown, the formulation containing the cleavable triglycine linker is more rapidly cleared.

EXAMPLE 8

Tumor Imaging

A. DSPE-PEG(2000)Maleimide-Mercaptoacetic Acid Adduct

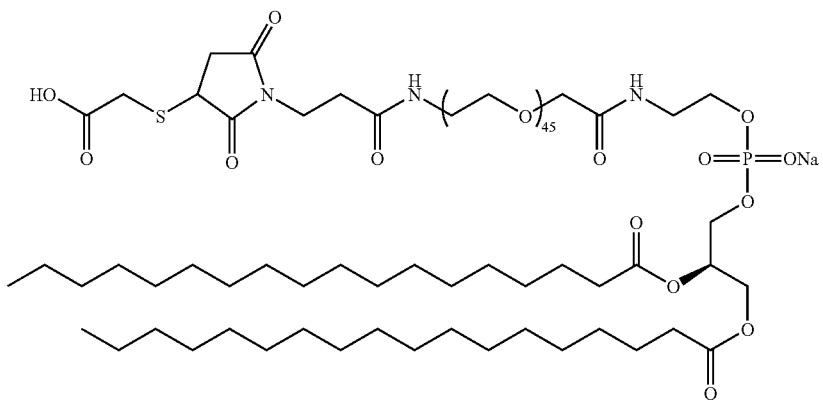

1,2-Distearoyl-sn-Glycero-3-Phosphoethanolamine-N-[Maleimide(Polyethylene Glycol)2000] is dissolved in DMF and degassed by sparging with nitrogen or argon. The oxygen-free solution is adjusted to pH 7-8 using DIEA, and treated with mercaptoacetic acid. Stirring is continued at ambient temperatures until analysis indicates complete consumption of starting materials. The solution is used directly in the following reaction.

B. Conjugation of the DSPE-PEG(2000)Maleimide-Mercaptoacetic Acid Adduct with Anti-Tumor Associated Antigen The product solution of Part A, above, is pre-activated by the addition of HBTU and sufficient DIEA to maintain pH 8-9. To the solution is added monoclonal antibody specific for tumor associated antigen, and the solution is stirred at room temperature under nitrogen for 18 h. DMF is removed in vacuo and the crude product is purified by preparative HPLC to obtain the PE coupled through a linker to anti-tumor antibodies.

C. Preparation of Nanoparticles:

The paramagnetic nanoparticles are produced as described in Flacke, S., et al., *Circulation* (2001) 104:1280-1285. Briefly, the nanoparticulate emulsions are comprised of 40% (v/v) perfluorooctylbromide (PFOB), 2% (w/v) of a surfactant co-mixture, 1.7% (w/v) glycerin and water representing the balance.

The surfactant of control, i.e., non-targeted, paramagnetic emulsions included 60 mole % lecithin (Avanti Polar Lipids, Inc., Alabaster, Ala.), 8 mole % cholesterol (Sigma Chemical Co., St. Louis, Mo.), 2 mole % dipalmitoyl-phosphatidylethanolamine (DPPE) (Avanti Polar Lipids, Inc., Alabaster, Ala.) and 30 mole % gadolinium diethylenetriaminepentaacetic acid-bisoleate (Gd-DTPA-BOA, Gateway Chemical Technologies, St. Louis, Mo.). The preparation of chelate is described in Example 1.

Tumor-targeted paramagnetic nanoparticles are prepared as above with a surfactant co-mixture that included: 60 mole % lecithin, 0.05 mole % of the conjugate of paragraph B, 8 mole % cholesterol, 30 mole % Example 1 chelate containing $Gd^{3+}$ and 1.95 mole % DPPE.

Tumor-targeted non-paramagnetic nanoparticles are prepared in an identical fashion to the targeted formulation excluding the addition of the lipophilic $Gd^{3+}$ chelate, which is substituted in the surfactant co-mixture with increased lecithin (70 mole %) and cholesterol (28 mole %).

The components for each nanoparticle formulation are emulsified in a M110S Microfluidics emulsifier (Microfluidics, Newton, Mass.) at 20,000 PSI for four minutes. The completed emulsions are placed in crimp-sealed vials and blanketed with nitrogen.

D. Tumor Model

Male New Zealand White Rabbits (~2.0 kg) are anesthetized with intramuscular ketamine and xylazine (65 and 13 mg/kg, respectively). The left hind leg of each animal is shaved, sterile prepped and infiltrated locally with Marcaine™ prior to placement of a small incision above the popliteal fossa. A 2 by 2 by 2 $mm^3$ Vx-2 carcinoma tumor fragment, freshly obtained from a donor animal, is implanted at a depth of approximately 0.5 cm. Anatomical planes are reapproximated and secured with a single absorbable suture. Finally, the skin incision is sealed with Dermabond skin glue. Following the tumor implantation procedure, the effects of xylazine are reversed with yohimbine and animals are allowed to recover.

Twelve days after Vx-2 implantation rabbits are anesthetized with 1% to 2% Isoflurane™, intubated, ventilated and positioned within the bore of the MRI scanner for study. Intravenous and intraarterial catheters, placed in opposite ears of each rabbit, are used for systemic injection of nanoparticles and arterial blood sampling as described below. Animals are monitored physiologically throughout the study in accordance with a protocol and procedures approved by the Animal Studies Committee at Washington University Medical School.

At 12 days post-implantation, Vx-2 tumor volumes of animals receiving tumor-targeted (130±39 $mm^3$) or non-targeted nanoparticles (148±36 $mm^3$) were not different (p>0.05).

Twelve New Zealand rabbits implanted with Vx-2 tumors, as described above, are randomized into three treatment regimens and received either:

1) tumor-targeted paramagnetic nanoparticles (tumor-targeted, n=4),
2) non-targeted paramagnetic nanoparticles (i.e., control group, n=4), or
3) tumor-targeted non-paramagnetic nanoparticles followed by tumor-targeted paramagnetic nanoparticles (i.e., competition group, n=4).

In treatment groups 1 and 2, rabbits receive 0.5 ml/kg of tumor-targeted or control paramagnetic nanoparticles following the acquisition of baseline MR images. In treatment group 3, all rabbits receive 0.5 ml/kg tumor-targeted non-paramagnetic nanoparticles two hours before MR imaging followed by 0.5 ml/kg tumor-targeted paramagnetic nanoparticles. Dynamic MR images are obtained at injection and every 30 minutes for each animal over two hours to monitor initial changes in signal enhancement in the tumor and muscle regions. All tumors are resected and frozen for histology to corroborate MR molecular imaging results.

E. Magnetic Resonance Imaging and Histology Procedures

Twelve days after tumor implantation, the animals undergo MRI scanning on a 1.5 Tesla clinical scanner (NT Intera with Master Gradients, Philips Medical Systems, Best, Netherlands). Each animal is placed inside a quadrature head/neck birdcage coil with an 11 cm diameter circular surface coil positioned against the hindlimb near the tumor. The quadrature body coil is used for all radio-frequency transmission; the birdcage coil is used for detection during scout imaging; and the surface coil is used for detection during high-resolution imaging. A 10 ml syringe filled with gadolinium diethylenetriaminepentaacetic acid (Gd-DTPA) doped water is placed within the high-resolution field of view (FOV) and served as a signal intensity standard.

Tumors are initially localized at the site of implantation with a $T_2$-weighted turbo spin-echo scan (TR: 2000 ms, TE: 100 ms, FOV: 150 mm, slice thickness: 3 mm, matrix: 128 by 256, signal averages: 2, turbo factor: 3, scan time: 3 min). A high-resolution, $T_1$-weighted, fat suppressed, three-dimensional, gradient echo scan (TR: 40 ms, TE: 5.6 ms, FOV: 64 mm, slice thickness: 0.5 mm, contiguous slices: 30, in-plane resolution: 250 μm, signal averages: 2, flip angle: 65°, scan time: 15 min) of the tumor is collected at baseline and repeated immediately and 30, 60, 90 and 120 minutes after paramagnetic nanoparticle injection.

Tumor volumes are calculated on an offline image processing workstation (EasyVision v5.1, Philips Medical Systems, Best, Netherlands). Regions-of-interest (ROI) were applied manually around the tumor in each slice of the $T_1$-weighted baseline scan, are combined into a three-dimensional object and the volume calculated.

To quantify image enhancement over time, an unbiased image analysis program is used. $T_1$-weighted images (three contiguous slices through the center of each tumor) collected before, immediately after and 30, 60, 90 and 120 minutes after intravenous nanoparticle injection are analyzed with MATLAB (The MathWorks, Inc., Natick, Mass.). The image intensity at each timepoint is normalized to the baseline image via the reference gadolinium standard. Serial images are spatially co-registered and contrast enhancement is determined for each pixel at each post-injection timepoint. An ROI is manually drawn around a portion of the hindlimb muscle in the baseline images and the average pixel-by-pixel signal enhancement inside the ROI is calculated at each timepoint. A second ROI is manually drawn around the tumor and the standard deviation of the tumor signal is calculated in the baseline image for each animal. Pixels are considered enhanced when signal intensity is increased by greater than three times the standard deviation of the tumor signal at baseline (i.e., enhancement greater than 99% of the variation seen at baseline). Solitary enhancing pixels, those in which all surrounding in-plane pixels do not enhance, are removed from the calculations as noise. The remaining enhancing pixel clusters are mapped back to the immediate, 30, 60 and 90 minute images and the average signal increase at each interval is determined. Statistical comparisons are performed for tumor and muscle for each timepoint using ANOVA (SAS, SAS Institute, Cary, N.C.). Treatment means are separated using the LSD procedure (p<0.05).

After imaging, tumors are resected for histology and immunohistochemistry to verify tumor pathology and assess associated vascularity and angiogenesis. Tumors are frozen (−78° C.) in OCT medium with known orientation relative to original anatomical position and the MRI image planes. Four micron frozen sections (Leica Microsystems, Inc., Bannockburn, Ill.), fixed in acetone at −20° C. for 15 minutes and air dried overnight (4° C.), are stained with hematoxylin-eosin, murine anti-human/rabbit endothelium antibody (QBEND/40, 1:10 dilution, Research Diagnostics, Inc., Flanders, N.J.), or a murine anti-human $\alpha_v\beta_3$-integrin (LM-609, 1:200 dilution, Chemicon International, Temecula, Calif.). Immunohistochemistry is performed using the Vectastain® Elite ABC kit (Vector Laboratories, Burlingame, Calif. 94010), developed with the Vector® VIP kit, counterstained with Vector® methylgreen nuclear counterstain. Slides are reviewed with a Nikon Eclipse E800 research microscope (Nikon USA, Melville, N.Y.) equipped with a Nikon digital camera (Model DXM 1200) and captured with Nikon ACT-1 software.

The invention claimed is:

1. A compound of the formula:

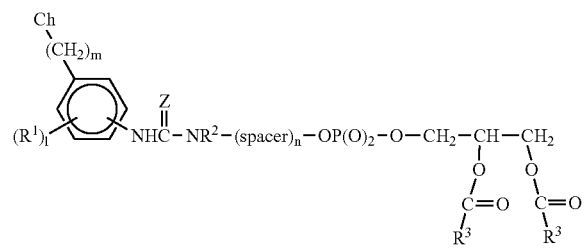

(1)

wherein Ch represents a chelating moiety comprising at least two nitrogens spaced by alkylene groups and to which carboxylic acid-bearing moieties are coupled;
m is 0-3;
each $R^1$ is independently a non-interfering substituent selected from the group consisting of halo, OR, $NR_2$, SR, CN, $NO_2$, $SO_3H$, and R where R is alkyl or alkenyl optionally substituted by halo, or =O, and optionally containing a heteroatom, such as O, S or N;
l is 0-2;
Z is S or O;
$R^2$ is H or alkyl (1-4C);
n is 1; and
each $R^3$ is independently an optionally substituted saturated or unsaturated hydrocarbyl group containing at least 10C, and
spacer is —$CH_2CH_2$— and/or includes a peptide, a pseudopeptide, or a polyalkylene glycol, optionally containing a cleavage site.

2. The compound of claim 1, wherein the spacer is $CH_2CH_2$ and $R^2$ is H.

3. The compound of claim 1, wherein Z is S.

4. The compound of claim 1, wherein $R^2$ is H.

5. The compound of claim 1, wherein l is 0 and m is 1 or 0.

6. The compound of claim 1, wherein each $R^3COO$ is a residue of a naturally occurring fatty acid or a mixture of said residues.

7. The compound of claim 1, wherein $R^1$ is $CH_3O$.

8. The compound of claim 1, wherein the spacer is a peptide or a polyalkylene glycol.

9. The compound of claim 1, which further comprises, associated with Ch, a paramagnetic metal ion or a radionuclide metal.

10. A composition which comprises the compound of claim 1 associated with lipophilic nanoparticles or microparticles.

11. A composition which comprises the compound of claim 9 associated with lipophilic nanoparticles or microparticles.

12. The composition of claim 10, wherein said particles contain at least 2,000 copies of the compound of claim 1.

13. The composition of claim 11, wherein said particles contain at least 2,000 copies of the compound of claim 9.

14. The composition of claim 10, wherein the nanoparticles or microparticles further contain a targeting agent.

15. The composition of claim 11, wherein the nanoparticles or microparticles further contain a targeting agent.

16. The composition of claim 14, wherein said targeting agent is a receptor ligand or an antibody or fragment thereof.

17. The composition of claim 15, wherein said targeting agent is a receptor ligand or an antibody or fragment thereof.

18. The composition of claim 10, wherein said microparticles or nanoparticles further comprise a biologically active agent.

19. The composition of claim 11, wherein said microparticles or nanoparticles further comprise a biologically active agent.

20. The composition of claim 10, wherein said microparticles or nanoparticles are liposomes, oil droplets, perfluorocarbon nanoparticles, lipid-coated protein particles, or lipid-coated polysaccharides.

21. The composition of claim 11, wherein said microparticles or nanoparticles are liposomes, oil droplets, perfluorocarbon nanoparticles, lipid-coated protein particles, or lipid-coated polysaccharides.

22. A method to obtain a magnetic resonance image or an image produced by a radionuclide which method comprises imaging a tissue which is associated with the composition of claim 11.

* * * * *